(12) United States Patent
Li et al.

(10) Patent No.: US 12,048,809 B2
(45) Date of Patent: Jul. 30, 2024

(54) AUXILIARY SPUTUM EXCRETION METHOD FOR NON-INVASIVE VENTILATOR AND NON-INVASIVE VENTILATOR

(71) Applicant: YAGUO INC., Beijing (CN)

(72) Inventors: Xiaomiao Li, Beijing (CN); Xiaoxue Li, Beijing (CN); Jingshi Xie, Beijing (CN)

(73) Assignee: YAGUO INC., Beijing (CN)

(*) Notice: Subject to any disclaimer, the term of this patent is extended or adjusted under 35 U.S.C. 154(b) by 942 days.

(21) Appl. No.: 17/086,415

(22) Filed: Nov. 1, 2020

(65) Prior Publication Data
US 2021/0046269 A1 Feb. 18, 2021

Related U.S. Application Data (63) Continuation of application No. PCT/CN2019/085157, filed on Apr. 30, 2019.

(30) Foreign Application Priority Data

May 2, 2018 (CN) .......................... 201810409032.5

(51) Int. Cl.
*A61M 16/00* (2006.01)

(52) U.S. Cl.
CPC ...... *A61M 16/022* (2017.08); *A61M 16/0003* (2014.02); *A61M 2016/0039* (2013.01);
(Continued)

(58) Field of Classification Search
CPC .......... A61M 16/0003; A61M 16/0006; A61M 16/022; A61M 2016/0039; A61M 2016/0042; A61M 2230/435
See application file for complete search history.

(56) References Cited

U.S. PATENT DOCUMENTS

| 8,460,223 B2* | 6/2013 | Huster | A61H 9/005 601/149 |
| 2002/0183642 A1* | 12/2002 | Murphy | A61B 5/061 600/529 |

(Continued)

FOREIGN PATENT DOCUMENTS

| CN | 102215891 | 10/2011 |
| CN | 202490292 | 10/2012 |

(Continued)

OTHER PUBLICATIONS

SIPO, First Office Action for CN Application No. 201810409032.5, Jul. 5, 2019.

(Continued)

*Primary Examiner* — Colin W Stuart
*Assistant Examiner* — Douglas Y Sul
(74) *Attorney, Agent, or Firm* — Hodgson Russ LLP (57) ABSTRACT

An auxiliary sputum excretion method for a non-invasive ventilator and the invasive ventilator, solving the technical problem of how to help a patient with non-invasive ventilation to excrete sputum. In the auxiliary sputum excretion method, a sputum excretion operation is initiated in each respiratory cycle of a patient after the non-invasive ventilator determines that the patient needs sputum excretion during a normal mechanical ventilation of the non-invasive ventilator for the patient, and the sputum excretion operation is stopped in response to determining that the patient needs to stop the sputum excretion.

16 Claims, 4 Drawing Sheets

(52) U.S. Cl.
CPC ............... *A61M 2016/0042* (2013.01); *A61M 2230/435* (2013.01)

(56) References Cited

U.S. PATENT DOCUMENTS

| | | | | |
|---|---|---|---|---|
| 2011/0220107 | A1* | 9/2011 | Kimm | ............... A61M 16/0051 128/204.21 |
| 2014/0150791 | A1* | 6/2014 | Birnkrant | ............... G16H 20/40 128/204.23 |
| 2015/0136134 | A1* | 5/2015 | Kissel | ............... A61M 16/0069 128/204.22 |
| 2015/0165144 | A1* | 6/2015 | Lee | ................... A61M 16/0003 128/204.23 |
| 2018/0243521 | A1* | 8/2018 | Lee | ................... A61M 16/0069 |
| 2019/0001092 | A1* | 1/2019 | Grashow | ............. A61M 16/202 |
| 2019/0142686 | A1* | 5/2019 | Lee | ........................ A61H 31/00 601/44 |

FOREIGN PATENT DOCUMENTS

| | | | |
|---|---|---|---|
| CN | 106139338 | | 11/2016 |
| CN | 106730193 | | 5/2017 |
| CN | 106730193 A | * | 5/2017 |
| CN | 108543182 | | 9/2018 |
| EP | 3127574 | | 2/2017 |
| WO | 2007054829 | | 5/2007 |

OTHER PUBLICATIONS

SIPO, Third Office Action for CN Application No. 201810409032.5, Mar. 16, 2020.
WIPO, ISR for PCT/CN2019/085157, Aug. 5, 2019.
EPO, Extended European Search Report for EP Application No. 19796074.3, Dec. 22, 2021.

* cited by examiner

AUXILIARY SPUTUM EXCRETION METHOD FOR NON-INVASIVE VENTILATOR AND NON-INVASIVE VENTILATOR

CROSS-REFERENCE TO RELATED APPLICATION

This application is a continuation of International Application No. PCT/CN2019/085157, filed on Apr. 30, 2019, which claims priority to Chinese Patent Application Serial No. 201810409032.5, filed on May 2, 2018, the entire disclosures of which are incorporated herein by reference.

FIELD

The present disclosure relates to a field of medical technology, and more particularly to an auxiliary sputum excretion method for a non-invasive ventilator and a non-invasive ventilator.

BACKGROUND

Medical positive-pressure ventilator can be roughly divided into two categories, invasive ventilators and non-invasive ventilators. The invasive ventilators need to establish artificial airways such as orotracheal or nasotracheal intubation, tracheostomy cannula, etc., to ventilate the patient through the artificial airway. The non-invasive ventilators usually use a mask to complete the function of mechanical ventilation.

Clinically, for patients with non-invasive ventilator, it mainly depends on the patient's own ability to clear airway sputum. When the expectoration ability is insufficient, it can only be switched from non-invasive ventilation to invasive ventilation.

Therefore, how to help patients with non-invasive ventilation to excrete the sputum is an urgent clinical problem.

SUMMARY

Embodiments of the present disclosure provides an auxiliary sputum excretion method for a non-invasive ventilator, including: initiating a sputum excretion operation in each respiratory cycle of a patient after the non-invasive ventilator determines that the patient needs sputum excretion during a normal mechanical ventilation of the non-invasive ventilator for the patient; and stopping the sputum excretion operation in response to determining that the patient needs to stop the sputum excretion.

Embodiments of the present disclosure provide a non-invasive ventilator, including an inspiratory branch and an expiratory branch, and further including: a positive-pressure air supply arranged on the inspiratory branch; a negative-pressure air supply arranged on the expiratory branch; a sensor unit configured to monitor physiological data for determining whether a patient needs sputum excretion and whether the patient needs to stop sputum excretion; and a control unit, communicated and connected with the positive-pressure air supply, the negative-pressure air supply, and the sensor unit, and configured to: determine whether the patient needs sputum excretion and whether the patient needs to stop the sputum excretion by analyzing the physiological data monitored by the sensor unit, in response to determining that the patient needs the sputum excretion, control the positive-pressure air supply to apply a positive-pressure ventilation pressure for sputum excretion to airway of the patient or to fill lungs of the patient with a positive-pressure inspiratory tidal volume for sputum excretion every time the patient being in an inspiratory stage, and control the negative-pressure air supply to apply a negative-pressure ventilation pressure for sputum excretion to the airway of the patient every time the patient being in an expiratory stage, and stop the positive-pressure air supply applying the positive-pressure ventilation pressure for sputum excretion to the airway of the patient or filling the lungs of the patient with the positive-pressure inspiratory tidal volume for sputum excretion every time the patient being in the inspiratory stage, and stop the negative-pressure air supply applying the negative-pressure ventilation pressure for sputum excretion to the airway of the patient every time the patient being in the expiratory stage in response to determining that the patient needs to stop the sputum excretion.

Embodiments of the present disclosure provide a non-transitory computer storage medium, having auxiliary sputum excretion programs for a non-invasive ventilator. When the auxiliary sputum excretion programs for a non-invasive ventilator is executed by a processor, the auxiliary sputum excretion method for a non-invasive ventilator according to the first aspect is implemented. Additional aspects and advantages of embodiments of present disclosure will be given in part in the following descriptions, become apparent in part from the following descriptions, or be learned from the practice of the embodiments of the present disclosure.

BRIEF DESCRIPTION OF THE DRAWINGS

Above and/or additional aspects and advantages of embodiments of the present disclosure will become apparent and more readily appreciated from the following descriptions made with reference to the drawings, in which.

DESCRIPTIONS OF REFERENCE NUMERALS

1: patient interface air path; 2: inspiratory branch; 3: expiratory branch; 4: sensor unit; 5: control unit; 6: display and operation unit; 7: nebulizer unit; 8: intra-pulmonary percussive unit.

DETAILED DESCRIPTION

Reference will be made in detail to embodiments of the present disclosure. Examples of the embodiments of the present disclosure will be shown in drawings, in which the same or similar elements and the elements having same or similar functions are denoted by like reference numerals throughout the descriptions. The embodiments described herein according to drawings are explanatory and illustrative, not construed to limit the present disclosure.

Medical positive-pressure ventilator can be roughly divided into two categories, invasive ventilators and non-invasive ventilators. The invasive ventilators need to establish artificial airways such as orotracheal or nasotracheal intubation, tracheostomy cannula, etc., to ventilate the patient through the artificial airway. The non-invasive ventilators usually use a mask to complete the function of mechanical ventilation. Compared with the invasive ventilators, the non-invasive ventilators have the advantages of convenient to use, non-invasiveness, and easy weaning. Due to traumatic nature of invasive mechanical ventilation, following shortcomings may be brought. The patient is more likely to get ventilator-associated pneumonia (VAP), and it is more likely to cause the loss of physiological functions of the patient and to form ventilator dependence. Higher care level is required to be provided by the medical personnel. The normal physiological functions of the patient are damaged, and the patient is unable to communicate normally, which seriously affects the quality of life of the patient. Greater financial pressure is brought to the patient's family.

However, the problems with sputum excretion encountered by a patient who uses a non-invasive ventilator often lead the patient to switch to use an invasive ventilator. Specifically, a patient who use invasive and non-invasive ventilators often has the problems of weak respiratory muscles, unable to form an effective cough, and unable to clear the airway on his/her own. However, when the patient is ventilated with an invasive ventilator, the nursing personnel can complete the airway cleaning through artificial airway sputum suction. In contrast, currently, when a non-invasive ventilator is used for non-invasive ventilation, there is no ideal auxiliary means of sputum excretion. Clinically, it mainly depends on the patient's own sputum expectoration ability. When the expectoration ability is insufficient, it can only be switched from non-invasive ventilation to invasive ventilation.

Therefore, how to help patients with non-invasive ventilation to excrete the sputum is an urgent clinical problem. To solve this problem, the present disclosure provides an auxiliary sputum excretion method for a non-invasive ventilator and the non-invasive ventilator.

Embodiment One

An auxiliary sputum excretion method for a non-invasive ventilator provided by the present disclosure is detailed as: initiating a sputum excretion operation in each respiratory cycle of a patient after the non-invasive ventilator determines that the patient needs sputum excretion during a normal mechanical ventilation of the non-invasive ventilator for the patient; and stopping the action of initiating the sputum excretion operation in each respiratory cycle of the patient until the non-invasive ventilator determines that the patient needs to stop the sputum excretion.

With the auxiliary sputum excretion method for a non-invasive ventilator, a problem of helping a patient with non-invasive ventilation to excrete sputum is solved. Particularly when applying to a non-invasive ventilator, solving this problem may not only improve the success rate of non-invasive ventilation and reduce the number of invasive ventilation, but also improve the success rate of switching from invasive ventilation to non-invasive ventilation for a patient who is intubated. In this way, on the one hand, the care level of the patient with non-invasive ventilation may be greatly improved, and the survival rate and quality of life of the patient may be improved, and on the other hand, waste of medical resources and economic burden on the patient's family may be reduced.

Figure 1:
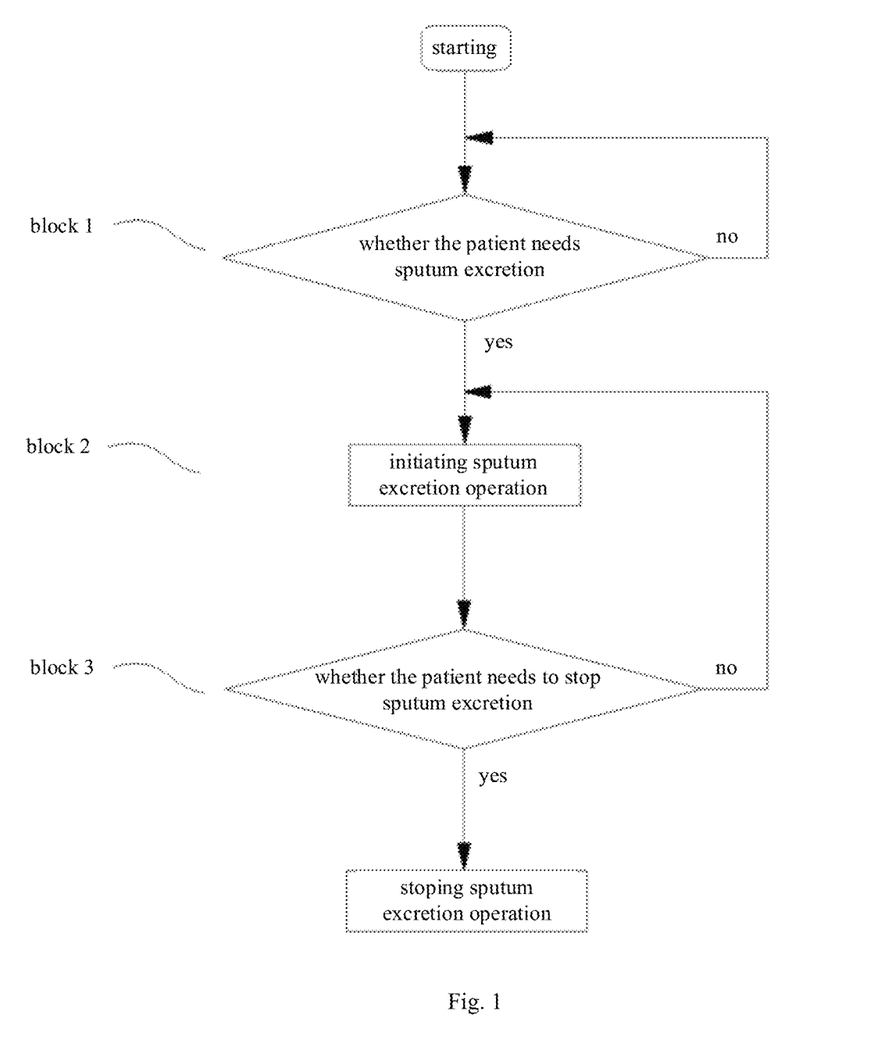
FIG. 1 is a flow chart of an auxiliary sputum excretion method for a non-invasive ventilator provided in following embodiment 1.

With reference to FIG. 1, in this embodiment, the non-invasive ventilator includes an inspiratory branch, an expiratory branch, and a patient interface air path. The inspiratory branch and the expiratory branch are respectively connected with the patient interface air path.

A normal mechanical ventilation mode of the non-invasive ventilator may be as follows. When the patient inhales, the inspiratory branch is on, the expiratory branch is off, a positive-pressure air supply provides an injection air flow, and positive-pressure air is injected into lungs of the patient through the inspiratory branch and the patient interface air path. When the patient exhales, the inspiratory branch is off, the expiratory branch is on, and the patient uses his own strength to expel the air in the lungs through the patient interface air path and the expiratory branch. The on and off of the inspiratory branch and the expiratory branch are implemented by corresponding valves.

An auxiliary sputum excretion method for a non-invasive ventilator may be particularly as performing following actions during the above normal mechanical ventilation process.

At block 1, the non-invasive ventilator determines whether the patient needs the sputum excretion. If yes, an action at block 2 is performed. Otherwise, the action at block 1 is repeated. In this embodiment, the non-invasive ventilator uses oxygen saturation, airway resistance, lung compliance, and breath sounds as criterions for determining whether the patient needs the sputum excretion. In detail, the following methods are used to determine whether the patient needs the sputum excretion.

The non-invasive ventilator monitors the oxygen saturation, the airway resistance, the lung compliance, and the breath sounds of the patient, and determines that the patient needs the sputum excretion in response to determining that a monitoring result of the oxygen saturation, the airway resistance, the lung compliance, and the breath sounds of the patient satisfies any one of following four conditions, i.e., condition A to condition D.

Condition A: the oxygen saturation of the patient decreases to a set value of oxygen saturation for initiating the sputum excretion, or decreases by an oxygen saturation change value for initiating the sputum excretion. The set value of oxygen saturation for initiating the sputum excretion may be preset by medical personnel, or may be an average value of the patient's oxygen saturation in a certain time period calculated by the non-invasive ventilator, or may be a value obtained by reducing a preset value based on an average value of the patient's oxygen saturation in a certain time period. The preset value and the above certain time period may be preset by medical personnel or may be preset in the non-invasive ventilator. For example, the set value of oxygen saturation for initiating the sputum excretion may be selected from a range of 80%-95%. Decreasing by the oxygen saturation change value for initiating the sputum excretion means decreasing the oxygen saturation change value for initiating the sputum excretion relative to a value monitored when starting to monitor the oxygen saturation of the patient. The oxygen saturation change value for initiating the sputum excretion may be preset by the medical personnel. For example, the oxygen saturation change value for initiating the sputum excretion may be selected from a range of 2%-10%.

Condition B: the airway resistance of the patient is greater than a normal airway resistance level by a set value of airway resistance for initiating the sputum excretion, and continues to be greater than the normal airway resistance level by the set value of airway resistance for initiating the sputum excretion for a certain time period. The normal airway resistance level of the patient is an average value of the patient's airway resistance in a certain period calculated by the non-invasive ventilator. The set value of airway resistance for initiating the sputum excretion and the certain time period may be preset by the medical personnel, or be preset in the non-invasive ventilator. For example, the set value of airway resistance for initiating the sputum excretion may be selected from a range of 5~30 ml/cmH2O.

Condition C: the lung compliance of the patient is less than a normal lung compliance level by a set value of lung compliance for initiating the sputum excretion, and continues to be less than the normal lung compliance level by the set value of lung compliance for initiating the sputum excretion for a certain time period. The normal lung compliance level of the patient is an average value of the patient's lung compliance in a certain period calculated by the non-invasive ventilator. The set value of lung compliance for initiating the sputum excretion and the certain time period may be preset by the medical personnel, or be preset in the non-invasive ventilator. For example, the set value of lung compliance for initiating the sputum excretion may be selected from a range of 5~30 ml/cmH2O.

Condition D: moist rales are detected, a time proportion of the moist rales in a respiratory cycle is greater than a set proportion of moist rales for initiating the sputum excretion, a frequency of the moist rales in different respiratory cycles is greater than a set frequency of moist rales for initiating the sputum excretion, and a value of the moist rales is greater than a set value of moist rales for initiating the sputum excretion. The set proportion of moist rales for initiating the sputum excretion, the set frequency of moist rales for initiating the sputum excretion, and the set value of moist rales for initiating the sputum excretion may be preset by the medical personnel or be preset in the non-invasive ventilator. For example, the set proportion of moist rales for initiating the sputum excretion may be 20%, and the set frequency of moist rales for initiating the sputum excretion may be 60%.

At block 2, the non-invasive ventilator stops the above normal mechanical ventilation, and the non-invasive ventilator starts a sputum excretion operation in each respiratory cycle of the patient. In this embodiment, the sputum excretion operation includes: applying a positive-pressure ventilation pressure for sputum excretion to airway of the patient or filling lungs of the patient with a positive-pressure inspiratory tidal volume for sputum excretion in an inspiratory stage, and applying a negative-pressure ventilation pressure for sputum excretion to the airway of the patient in an expiratory stage. In detail, when the patient inhales, the inspiratory branch is on, the expiratory branch is off, and the positive-pressure air supply provides an air flow. When the patient exhales, the expiratory branch is on, the inspiratory branch is off, a negative-pressure air supply provides a negative-pressure air flow. Thus, while the patient exhales through its own strength, the negative-pressure air flow generated by the negative-pressure air supply increases expiratory air flow of the patient, and brings out the sputum in the airway. In addition, providing a suitable tidal volume when inhaling is more conducive to sputum excretion.

At block 3, the non-invasive ventilator determines whether the patient needs to stop the sputum excretion. If yes, initiating the sputum excretion operation in each respiratory cycle of the patient is stopped, and the normal mechanical ventilation is restored. Otherwise, the action at block 2 is repeated.

In the above action at block 3, the oxygen saturation, the airway resistance, the lung compliance, and the breath sounds are used as criterions for determining whether the patient needs to stop the sputum excretion. In detail, the non-invasive ventilator determines whether the patient needs to stop the sputum excretion by followings.

The non-invasive ventilator monitors the oxygen saturation, the airway resistance, the lung compliance, and the breath sounds of the patient, and determines that the patient needs to stop the sputum excretion when all the following condition a to condition d are satisfied.

Condition a: the oxygen saturation of the patient is greater than or equal to a set value of oxygen saturation for stopping the sputum excretion. The set value of oxygen saturation for stopping the sputum excretion is greater than the above set value of oxygen saturation for initiating the sputum excretion. The set value of oxygen saturation for stopping the sputum excretion may be preset by the medical personnel, or may be an average value of the patient's oxygen saturation in a certain period calculated by the non-invasive ventilator. The certain period may be preset by the medical personnel or be preset in the non-invasive ventilator. For example, the set value of oxygen saturation for stopping the sputum excretion may be selected from a range of 80%-98%.

Condition b: the airway resistance of the patient reaches the normal airway resistance level. The airway resistance of the patient may greater than the normal airway resistance level before the sputum excretion. Therefore, the airway resistance of the patient may need to decrease to the normal airway resistance level. The normal airway resistance level of the patient refers to an average value of the patient's airway resistance in a certain period calculated by the non-invasive ventilator. The certain time period may be preset by the medical personnel, or be preset in the non-invasive ventilator.

Condition c: the lung compliance of the patient reaches the normal lung compliance level. The lung compliance of the patient may be less than the normal lung compliance level before the sputum excretion. Therefore, the lung compliance of the patient may need to increase to the normal lung compliance level. The normal lung compliance level of the patient refers to an average value of the patient's lung compliance in a certain period calculated by the non-invasive ventilator. The certain time period may be preset by the medical personnel, or be preset in the non-invasive ventilator.

Condition d: no moist rales is detected, or moist rales are detected and a proportion of the moist rales in a respiratory cycle is less than a set proportion of moist rales for stopping the sputum excretion, or moist rales are detected and a frequency of the moist rales in different respiratory cycles is less than a set frequency of moist rales for stopping the sputum excretion, or moist rales are detected and a value of the moist rales is less than a set value of moist rales for stopping the sputum excretion. All of the set proportion of moist rales for stopping the sputum excretion, the set frequency of moist rales for stopping the sputum excretion, and the set value of moist rales for stopping the sputum excretion may be preset by the medical personnel, or be preset in the non-invasive ventilator. At the same time, it may be ensured that, the set proportion of moist rales for stopping the sputum excretion is less than the above-mentioned set proportion of moist rales for initiating the sputum excretion, the set frequency of moist rales for stopping the sputum excretion is less than the above-mentioned set frequency of moist rales for initiating the sputum excretion, and the set value of moist rales for stopping the sputum excretion is less than the above-mentioned set value of moist rales for initiating the sputum excretion. For example, the set proportion of moist rales for stopping the sputum excretion may be 5%, and the set frequency of moist rales for stopping the sputum excretion may be 20%.

In addition to satisfying the above conditions a-d to stop the sputum excretion, the non-invasive ventilator may also stop the sputum excretion through timing or manual operations. The non-invasive ventilator may set an upper time limit for stopping the sputum excretion. When a duration after initiating the sputum excretion is greater than the upper time limit for stopping the sputum excretion, regardless of whether other conditions are satisfied, the non-invasive ventilator may determine that the patient needs to stop the sputum excretion immediately. The upper time limit for stopping the sputum excretion may be preset by the medical personnel, or be preset in the non-invasive ventilator. For example, the upper time limit for stopping the sputum excretion may be select from a range of 30 s-120 s. In addition, the above-mentioned duration after initiating the sputum excretion refers to the total time of starting the sputum excretion in continuous respiratory cycles.

After that, the non-invasive ventilator may be restored to only perform normal mechanical ventilation for the patient.

Therefore, the auxiliary sputum excretion method for a non-invasive ventilator according to this embodiment has the following advantages compared with the use of traditional mechanical insufflation-exsufflation equipment. First, the needs for sputum excretion of the patient may be determined automatically, reducing the subjective factors of manual judgment, more real-time, and reducing the workload of medical personnel. Second, there is no need to remove the non-invasive ventilator during sputum excretion, reducing interference with the mechanical ventilation. Third, the auxiliary sputum excretion method is integrated in the ventilator, thus the sputum-excretion parameters can be linked with the respiratory parameters, reducing the barotrauma caused by the unreasonable settings of the sputum-excretion parameters.

Embodiment Two

Figure 2:
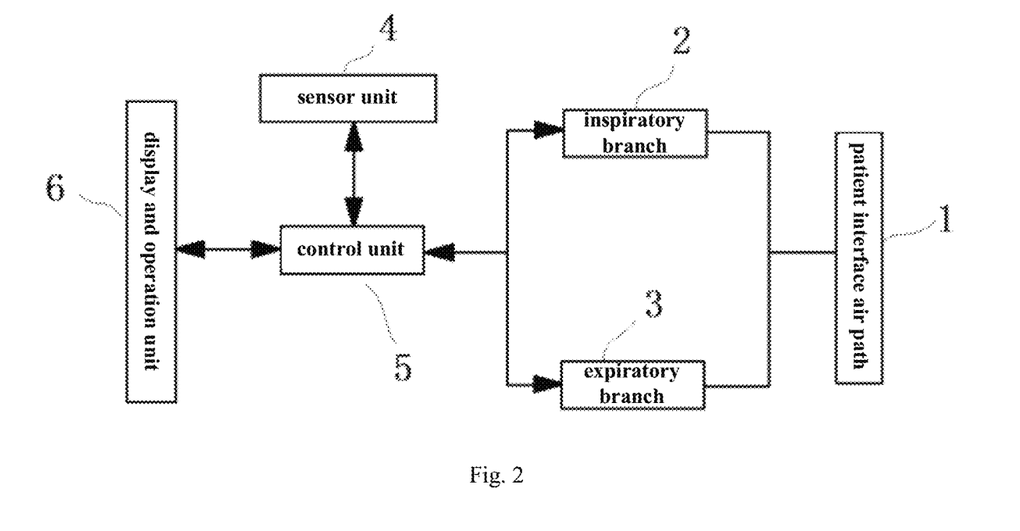
FIG. 2 is a schematic diagram of a non-invasive ventilator provided in following embodiment 2.

With reference to FIG. 2, a non-invasive ventilator is provided in this embodiment. The non-invasive ventilator may be applied to the auxiliary sputum excretion method for a non-invasive ventilator provided in embodiment one.

The non-invasive ventilator includes an inspiratory branch 2, an expiratory branch 3, a patient interface air path 1, a display and operation unit 6, a control unit 5, a sensor unit 4, a positive-pressure air supply (not shown in FIG. 2), and a negative-pressure air supply (not shown in FIG. 2).

The positive-pressure air supply is arranged on the inspiratory branch 2. The negative-pressure air supply is arranged on the expiratory branch 3.

The sensor unit 4 is able to monitor physiological data for determining whether a patient needs sputum excretion and whether the patient needs to stop sputum excretion. In this embodiment, the sensor unit 4 include a pressure sensor and a flow sensor arranged on the inspiratory branch 2, a pressure sensor and a flow sensor arranged on the expiratory branch 3, and a pressure sensor and a flow sensor arranged on the patient interface air path 1. Physiological data monitored by the above pressure sensors and flow sensors are pressures and flow values in the inspiratory branch 2, the expiratory branch 3, and the patient interface air path 1, to be used for obtaining lung compliance and airway resistance of the patient. The sensor unit 4 further includes an oxygen saturation sensor, configured to monitor physiological data of oxygen saturation of the patient in real time. The sensor unit 4 also includes a breath-sounds sensor, configured to monitor physiological data of breath sounds of the patient in real time.

The control unit 5 is communicated and connected with the positive-pressure air supply, the negative-pressure air supply, and the sensor unit 4 including the respective pressure sensors, the respective flow sensors, the oxygen saturation sensor, and the breath-sounds sensor. The control unit 5 is able to control the inspiratory branch 2 on, control the expiratory branch 3 off, and start the positive-pressure air supply to generate an injection air flow when the patient inhales. In this way, the injection air flow may inject positive-pressure air into lungs of the patient through the inspiratory branch 2 and the patient interface air path 1. The control unit 5 is able to control the inspiratory branch 2 off and control the expiratory branch 3 on when the patient exhales. In this way, the patient uses his own strength to expel the air in the lungs through the patient interface air path 1 and the expiratory branch 3. The control unit 5 is further able to determine whether the patient needs sputum excretion and whether the patient needs to stop the sputum excretion by analyzing the physiological data monitored by the respective sensors of the sensor unit 4, control normal mechanical ventilation to stop in response to determining that the patient needs the sputum excretion. The control unit 5 is able to, every time the patient being in an inspiratory stage, control the inspiratory branch 2 on and control the expiratory branch 3 off, and control the positive-pressure air supply to apply a positive-pressure ventilation pressure for sputum excretion to airway of the patient or to fill lungs of the patient with a positive-pressure inspiratory tidal volume for sputum excretion. The control unit 5 is able to, every time the patient being in an expiratory stage, control the expiratory branch 3 on and control the inspiratory branch 2 off, and control the negative-pressure air supply to apply a negative-pressure ventilation pressure for sputum excretion to the airway of the patient. The control unit 5 is able to stop the above-mentioned sputum excretion operations performed during the inspiratory stages and the expiratory stages of the patient in response to determining that the patient needs to stop the sputum excretion, and control the normal mechanical ventilation to be restored. The control unit 5 controls the on and off of the inspiratory branch 2 and the expiratory branch 3 by controlling on and off of corresponding valves.

In detail, in this embodiment, the control unit 5 may obtain the monitoring values of each pressure sensor, each flow sensor, the oxygen saturation sensor and the breath-sounds sensor, and obtains oxygen saturation, breath sounds, airway resistance, and lung compliance of the patient through analysis and calculation.

In this embodiment, the control unit 5 uses the oxygen saturation, the airway resistance, the lung compliance, and the breath sounds as a criterion for determining whether the patient needs the sputum excretion, and detailed determination conditions are the same as the condition A-condition D in the embodiment 1, which will not be repeated herein. The control unit 5 uses the oxygen saturation, the airway resistance, the lung compliance, and the breath sounds as a criterion for determining whether the patient needs to stop the sputum excretion, and detailed determination conditions are the same as the condition a-condition d in the embodiment 1, which will not be repeated herein.

The display and operation unit 6 is communicated and connected with the control unit 5. The display and operation unit 6 is for the medical personnel to input information.

The above-mentioned control unit 5 may be an integrated central processing unit, or may be dispersed into multiple control modules.

It should be understood that, working modes of the non-invasive ventilator includes a breathing support mode and a sputum excretion mode. The control unit 5 may control the working mode of the non-invasive ventilator to be the breathing support mode or the sputum excretion mode according to its own judgment result.

The breathing support mode is a mode of non-invasive ventilators in the prior art, which is used for normal mechanical ventilation of patients. In the breathing support mode, the respiratory parameters of the patient can be set, including inspiratory time, expiratory time, inspiratory pressure, an end-expiratory pressure, a tidal volume, etc.

In the sputum excretion mode, the non-invasive ventilator stops performing the normal mechanical ventilation for the patient, and performs a sputum excretion operation. In the sputum excretion mode, independent parameters for the sputum excretion operation may be set, including a value of a negative pressure, a tidal volume, the number of sputum excretions during the sputum excretion, etc. Alternatively, some parameters may also be set to be proportional to parameters in the breathing support mode. For example, the tidal volume during the sputum excretion is 1.0 to 2.0 times the tidal volume in the breathing support mode, the inspiratory pressure during the sputum excretion is 1.0 to 2.0 times the inspiratory pressure in the breathing support mode, and the inspiratory time during the sputum excretion is 1.0 to 2.0 times the inspiratory time in the breathing support mode.

The working modes of the non-invasive ventilator in this embodiment is described in detail as follows.

When the sputum excretion is not required, the non-invasive ventilator provides the normal mechanical ventilation for the patient, i.e., the breathing support mode.

Three ways for initiating the sputum excretion are as follows.

The first way is manual initiating. The medical personnel initiates the sputum excretion mode through a control interface of the display and operation unit 6, and can directly enter the sputum excretion operation.

The second way is periodical initiating. The sputum excretion operation is started based on a preset cycle.

The third way is initiating as needed. The control unit 5 determines that the patient needs the sputum excretion through oxygen saturation monitoring, breath-sounds monitoring (including lung rales monitoring) and patient breathing mechanics monitoring (the lung compliance and the airway resistance).

The above three ways for initiating the sputum excretion can exist simultaneously. Alternatively, the periodical initiating and the manual initiating can be added on the basis of initiating as needed.

Sputum excretion operation: During the sputum excretion, in each respiratory cycle, in the inspiratory stage, the control unit 5 controls the inspiratory branch 2 on, controls the expiratory branch 3 off, and controls the positive-pressure air supply to generate a positive-pressure injection air flow. Positive-pressure air is injected into the lungs of the patient through the inspiratory branch 2 and the patient interface air path 1. A positive-pressure ventilation pressure for sputum excretion is applied to the airway of the patient or lungs of the patient is filled with a positive-pressure inspiratory tidal volume for sputum excretion. In the expiratory stage, the inspiratory branch 2 is off, and the expiratory branch 3 is on. The control unit 5 controls the negative-pressure air supply to generate a negative-pressure air flow. A negative-pressure ventilation pressure for sputum excretion is applied to the airway of the patient. When the patient exhales through its own strength, the negative-pressure air supply generates the negative-pressure air flow, which increases expiratory air flow of the patient and brings out the sputum in the airway.

Stopping of the sputum excretion: the sputum excretion may be stopped with following conditions.

Manually stopping: an operator manually stops the sputum excretion.

Stopping by time setting: the sputum excretion is stopped when the duration of the sputum excretion operation reaches a preset time period.

Stopping as needed: the control unit 5 determines that the sputum excretion of the patient is completed by means of the oxygen saturation monitoring, the breath-sounds monitoring (including lung rales monitoring), and patient breathing mechanics monitoring (the lung compliance and the airway resistance), etc.

The above-mentioned three ways for stopping the sputum excretion may exist simultaneously. Alternatively, the manually stopping and the stopping by time setting can be added on the basis of the stopping as needed. The stopping by time setting may be preferably executed. That is, the final duration of each sputum excretion operation may not exceed the specified set time, so as to prevent the long-term sputum excretion operation from causing injure to the patient.

In conclusion, the non-invasive ventilator in this embodiment solves the problem of assisting the patient with non-invasive ventilation to discharge sputum. Solving this problem may not only reduce the number of invasive ventilation, but also improve the success rate of switching from invasive ventilation to non-invasive ventilation for a patient who is intubated. In this way, on the one hand, the level of care for the patient with non-invasive ventilation may be greatly improved, and the survival rate and quality of life of the patient may be improved. On the other hand, waste of medical resources and economic burden on the patient's family may be reduced. In addition, the non-invasive ventilator of this embodiment still provides positive pressure for the patient while excrete the sputum, ensuring normal mechanical ventilation effect, and can continuously excrete the sputum.

Embodiment Three

Figure 3:
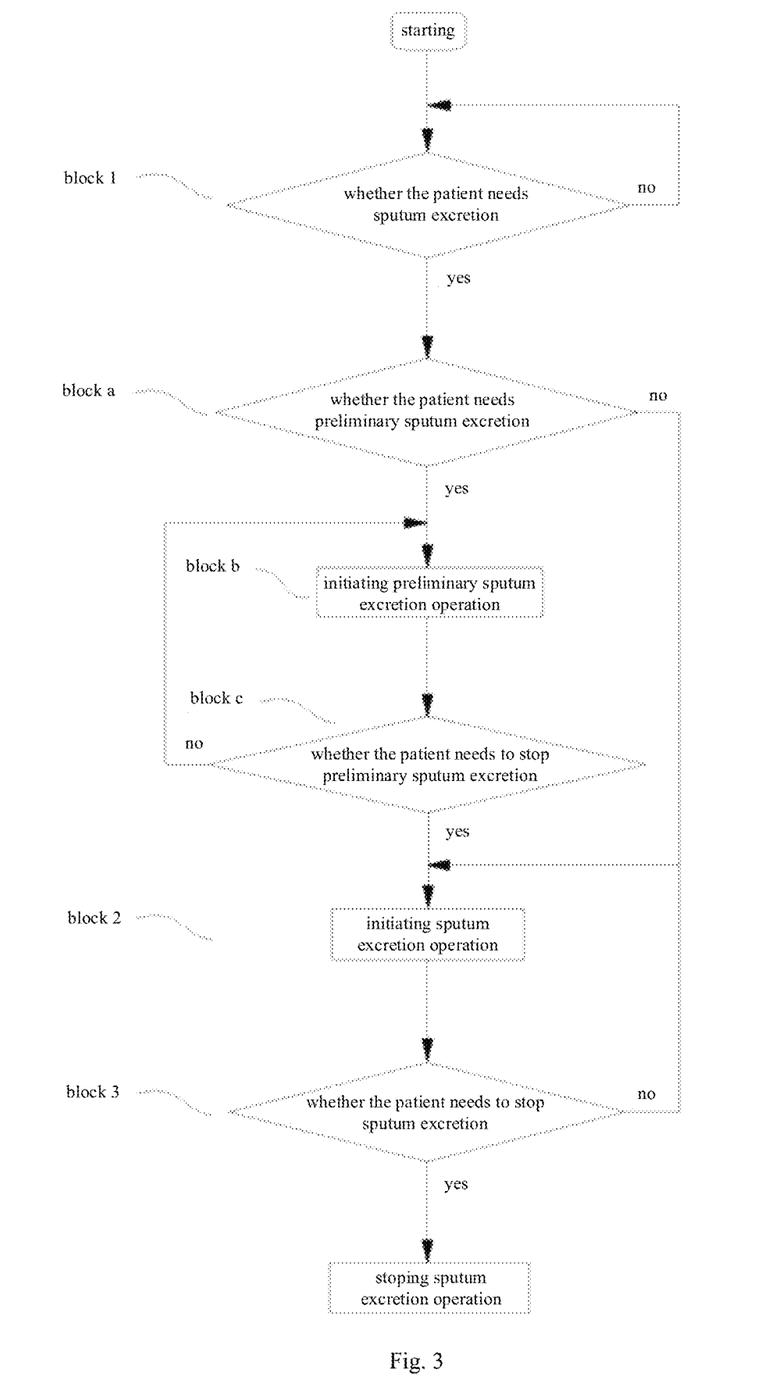
FIG. 3 is a flow chart of an auxiliary sputum excretion method for a non-invasive ventilator provided in following embodiment 3.

In this embodiment, determining and operation of preliminary sputum excretion are added on the basis of embodiment one. That is, the non-invasive ventilator determines whether a patient needs the preliminary sputum excretion after determining that the patient needs the sputum excretion. The preliminary sputum excretion operation is performed after the non-invasive ventilator determines that the patient needs the preliminary sputum excretion, and the preliminary sputum excretion operation is stopped until the non-invasive ventilator determines that the patient needs to stop the preliminary sputum excretion, and initiating the sputum excretion operation in each respiratory cycle of the patient is performed. The non-invasive ventilator directly initiate the sputum excretion operation in each respiratory cycle of the patient.

In detail, with reference to FIG. 3, in this embodiment, the auxiliary sputum excretion method for a non-invasive ventilator may be performing following actions during normal mechanical ventilation, detailed as followings.

At block 1, the non-invasive ventilator determines whether the patient needs the sputum excretion. If yes, an action at block a is performed. Otherwise, the action at block 1 is repeated. The determining method may be the same as that of embodiment one, and will not be repeated.

At block a, the non-invasive ventilator determines whether the patient needs the preliminary sputum excretion. If yes, an action at block b is performed. Otherwise, an action at block 2 is performed. The non-invasive ventilator uses breath sounds as a criterion for determining whether the patient needs the preliminary sputum excretion. That is, the non-invasive ventilator determines that the patient needs the preliminary sputum excretion through a following way.

The breath sounds of the patient is monitored. It is determined that the patient needs the preliminary sputum excretion when medium moist rales is detected, and a time proportion of the medium moist rales in a respiratory cycle is greater than a set proportion of medium moist rales for initiating the preliminary sputum excretion, and a frequency of the medium moist rales in different respiratory cycles is greater than a set frequency of medium moist rales for initiating the preliminary sputum excretion, and a value of the medium moist rales is greater than a set value of medium moist rales for initiating the preliminary sputum excretion, and no coarse moist rales is detected. Alternatively, it is determined that the patient needs the preliminary sputum excretion when fine moist rales is detected, and a time proportion of the fine moist rales in a respiratory cycle is greater than a set proportion of fine moist rales for initiating the preliminary sputum excretion, and a frequency of the fine moist rales in different respiratory cycles is greater than a set frequency of fine moist rales for initiating the preliminary sputum excretion, a value of the fine moist rales is greater than a set value of fine moist rales for initiating the preliminary sputum excretion, and no coarse moist rales is detected. The set proportion of medium moist rales for initiating the preliminary sputum excretion, the set frequency of medium moist rales for initiating the preliminary sputum excretion, the set value of medium moist rales for initiating the preliminary sputum excretion, the set proportion of fine moist rales for initiating the preliminary sputum excretion, the set frequency of fine moist rales for initiating the preliminary sputum excretion, and the set value of fine moist rales for initiating the preliminary sputum excretion are preset by medical personnel or pre-set in the non-invasive ventilator.

At block b, the non-invasive ventilator performs the preliminary sputum excretion operation. A main purpose of the preliminary sputum excretion operation is to make the sputum easier to discharge during subsequent sputum excretion. In this embodiment, the preliminary sputum excretion operation includes intrapulmonary percussion. The sputum is loosened by the intrapulmonary percussion and moves from a deep part of the lungs to a direction close to a main airway. The preliminary sputum excretion operation also includes a nebulization operation, which improve fluidity of the sputum and move from the deep part of the lungs to the direction close to the main airway.

At block c, the non-invasive ventilator determines whether the patient needs to stop the preliminary sputum excretion. If yes, the action at block 2 is performed. Otherwise, the action at block b is repeated. The non-invasive ventilator uses oxygen saturation, airway resistance, and breath sounds as criterions for determining whether the patient needs to stop the preliminary sputum excretion. In detail, in this embodiment, the non-invasive ventilator determines that the patient needs to stop the preliminary sputum excretion by the following means.

The non-invasive ventilator monitors the oxygen saturation, the airway resistance, and the breath sounds of the patient, and determines that the patient needs to stop the preliminary sputum excretion when any one of following condition I to condition III is satisfied.

Condition I: the oxygen saturation of the patient is less than a set value of oxygen saturation for stopping the preliminary sputum excretion. The set value of oxygen saturation for stopping the preliminary sputum excretion is less than the above-mentioned set value of oxygen saturation for initiating the sputum excretion. The set value of oxygen saturation for stopping the preliminary sputum excretion is preset by the medical personnel or preset in the non-invasive ventilator. For example, the set value of oxygen saturation for stopping the preliminary sputum excretion may be selected from a range of 80%-95%, and at the same time ensuring to be smaller than the above-mentioned set value of oxygen saturation for initiating the sputum excretion.

Condition II: the airway resistance of the patient is increased by a set increment of airway resistance for stopping the preliminary sputum excretion compared with airway resistance when determining that the patient needs the sputum excretion. The airway resistance when the patient needs the sputum excretion is airway resistance of the patient when it is determined that the patient needs the sputum excretion in the action at block 1. The airway resistance when the patient needs the sputum excretion is recorded by the non-invasive ventilator. The set increment of airway resistance for stopping the preliminary sputum excretion may be preset by the medical personnel or preset in the non-invasive ventilator. For example, the set increment of airway resistance for stopping the preliminary sputum excretion may be 20 cmH2O/L/min.

Condition III: coarse moist rales is detected, a time proportion of the coarse moist rales in a respiratory cycle is greater than a set proportion of coarse moist rales for stopping the preliminary sputum excretion, a frequency of the coarse moist rales in different respiratory cycles is greater than a set frequency of coarse moist rales for stopping the preliminary sputum excretion, and a value of the coarse moist rales is greater than a set value of coarse moist rales for stopping the preliminary sputum excretion. The set proportion of coarse moist rales for stopping the preliminary sputum excretion, the set frequency of coarse moist rales for stopping the preliminary sputum excretion, and the set value of coarse moist rales for stopping the preliminary sputum excretion may be preset by the medical personnel or preset in the non-invasive ventilator. For example, the set proportion of coarse moist rales for stopping the preliminary sputum excretion is 20%, and the set frequency of coarse moist rales for stopping the preliminary sputum excretion is 60%.

The non-invasive ventilator may further set an upper time limit for stopping the preliminary sputum excretion. It is determined that the patient needs to stop the preliminary sputum excretion in response to determining that a duration after initiating the preliminary sputum excretion is greater than the upper time limit for stopping the preliminary sputum excretion. The upper time limit for stopping the preliminary sputum excretion may be preset by the medical personnel or preset in the non-invasive ventilator. For example, the upper time limit for stopping the preliminary sputum excretion may be selected from a range of 1-30 min.

At block 2, the non-invasive ventilator stops the normal mechanical ventilation, and the non-invasive ventilator starts a sputum excretion operation in each respiratory cycle of the patient. In this embodiment, the sputum excretion operation includes: applying a positive-pressure ventilation pressure for sputum excretion to airway of the patient or filling lungs of the patient with a positive-pressure inspiratory tidal volume for sputum excretion in an inspiratory stage, and applying a negative-pressure ventilation pressure for sputum excretion to the airway of the patient in an expiratory stage.

At block 3, the non-invasive ventilator determines whether the patient needs to stop the sputum excretion. If yes, initiating the sputum excretion operation in each respiratory cycle of the patient is stopped. Otherwise, the action at block 2 is repeated. Details are the same as that of embodiment one, and will not repeat herein.

In conclusion, the non-invasive ventilator in this embodiment solves the clinical problem faced when assisting the patient with non-invasive ventilation to discharge sputum. Solving this problem may not only reduce the number of invasive ventilation, but also improve the success rate of switching from invasive ventilation to non-invasive ventilation for a patient who is intubated. In this way, on the one hand, the level of care for the patient with non-invasive ventilation may be greatly improved, and the survival rate and quality of life of the patient may be improved. On the other hand, waste of medical resources and economic burden on the patient's family may be reduced. In addition, combined with the preliminary sputum excretion operation, it can make subsequent sputum excretion of the patient smoother and reduce the number of sputum excretion operations. In addition, the non-invasive ventilator of this embodiment provides positive pressure for the patient while excrete the sputum, still ensuring the normal mechanical ventilation effect, and can continuously excrete the sputum.

Embodiment Four

Figure 4:
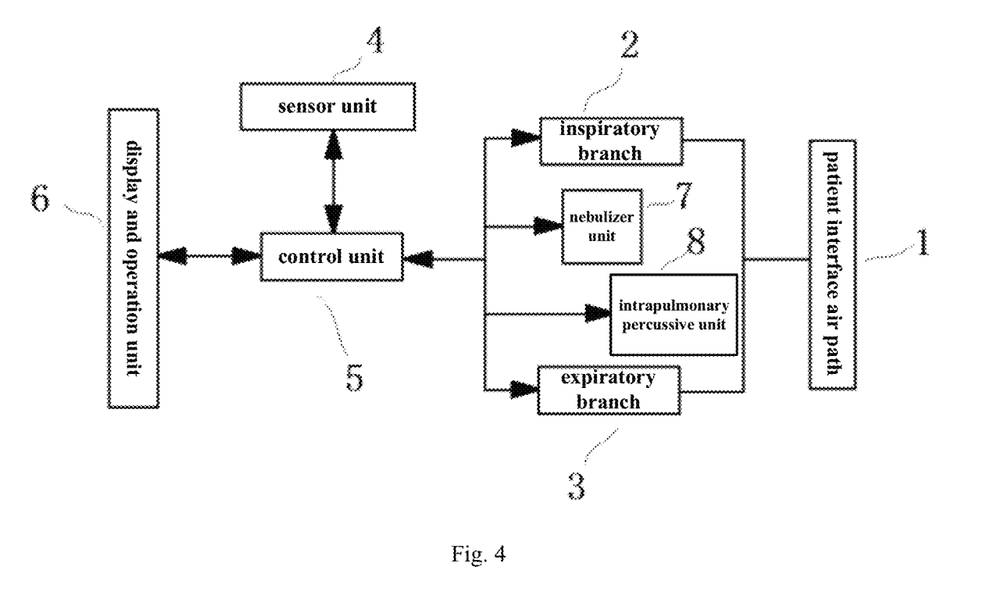
FIG. 4 is a schematic diagram of a non-invasive ventilator provided in following embodiment 4.

With reference to FIG. 4, a non-invasive ventilator of this embodiment may be applied to the auxiliary sputum excretion method for a non-invasive ventilator provided in embodiment three. Determining and operation of preliminary sputum excretion are added on the basis of embodiment two.

In detail, the non-invasive ventilator in this embodiment further includes a nebulizer unit 7 and an intrapulmonary percussive unit 8. The nebulizer unit 7 and the intrapulmonary percussive unit are communicated and connected with the control unit 5.

The control unit 5 is further able to perform analysis based on physiological data monitored by the sensor unit 4, determine whether the patient needs the preliminary sputum excretion or whether the patient needs to stop the preliminary sputum excretion, determine whether the patient needs the preliminary sputum excretion after determining that the patient needs the sputum excretion, start the nebulizer unit 7 and the intrapulmonary percussive unit 8 after determining that the patient needs the preliminary sputum excretion, and stop the working of the nebulizer unit 7 and the intrapulmonary percussive unit 8, stop the normal mechanical ventilation, and start the sputum excretion operation until it is determined that the patient needs to stop the preliminary sputum excretion. The control unit 5 directly stops the normal mechanical ventilation and starts the sputum excretion operation after determining that the patient does not need the preliminary sputum excretion.

That the control unit 5 determines whether the sputum excretion is needed and whether to stop the sputum excretion may be the same as that in embodiment two, and will not be repeated.

The control unit 5 determines that the patient needs the preliminary sputum excretion when medium moist rales or fine moist rales is detected, a time proportion of the medium moist rales or the fine moist rales in a respiratory cycle is greater than a set proportion of medium moist rales or fine moist rales for initiating the preliminary sputum excretion, a frequency of the medium moist rales or the fine moist rales in different respiratory cycles is greater than a set frequency of medium moist rales or fine moist rales for initiating the preliminary sputum excretion, a value of the medium moist rales or the fine moist rales is greater than a set value of medium moist rales or fine moist rales for initiating the preliminary sputum excretion, and no coarse moist rales is detected. Then the nebulizer unit 7 and the intrapulmonary percussive unit 8 are controlled to be started. The control unit 5 determines that the patient does not need the preliminary sputum excretion when the breath sounds of the patient do not contain the medium moist rales or the fine moist rales.

The control unit 5 determines that the patient needs to stop the preliminary sputum excretion when any one of the above condition I to condition III is satisfied, and will not be repeated. The control unit 5 controls the nebulizer unit 7 and the intrapulmonary percussive unit 8 off when determining the need to stop the preliminary sputum excretion, and start the sputum excretion operation at the same time.

In a sputum excretion mode of the non-invasive ventilator, the non-invasive ventilator stops performing the normal mechanical ventilation for the patient, and performs the sputum excretion operation, and alternatively performs the preliminary sputum excretion operation before stopping the normal mechanical ventilation.

The working modes of the non-invasive ventilator of this embodiment is described in detail as follows.

When the sputum excretion is not required, the non-invasive ventilator provides the normal mechanical ventilation for the patient, i.e., a breathing support mode. There are following three ways to start the sputum excretion.

The first way is manual initiating. The medical personnel initiates the sputum excretion mode through a control interface of the display and operation unit 6, and can directly enter the sputum excretion operation, or enter the preliminary sputum excretion operation first.

The second way is periodical initiating. The sputum excretion operation is started based on a preset cycle. The preliminary sputum excretion operation may be alternatively started.

The third way is initiating as needed. The control unit 5 determines that the patient needs the sputum excretion through oxygen saturation monitoring, breath-sounds monitoring (including lung rales monitoring) and patient breathing mechanics monitoring (the lung compliance and the airway resistance). Further, whether to start the preliminary sputum excretion is determined based on results of judgment.

Preliminary sputum excretion: in a preliminary sputum excretion stage, a nebulization operation and an intrapulmonary percussion operation are added on the basis of maintaining the normal mechanical ventilation. The nebulization and the intrapulmonary percussion may be started at the same time, but durations of the nebulization and the intrapulmonary percussion may be different. The medicine for the nebulization therapy is prepared in advance by medical personnel, and the speed and dosage of the nebulization are set. The nebulization is stopped when a nebulization dosage reaches a set value. The intrapulmonary percussion may be set by the operator to be implemented in an inspiratory stage, an expiratory stage, or a breath-holding stage, or be implemented in any combination of the above stages. An intensity and a percussion frequency of the intrapulmonary percussion may be set by the operator.

Stopping of the preliminary sputum excretion: there are following three ways to stop the preliminary sputum excretion.

Manually stopping: an operator manually stops the preliminary sputum excretion or start the sputum excretion operation.

Stopping by time setting: the preliminary sputum excretion stage is ended and the sputum excretion stage is entered when a preset time is reached.

Stopping as needed: the control unit 5 determines that purpose of the preliminary sputum excretion is achieved by means of the oxygen saturation monitoring, the breath-sounds monitoring (including lung rales monitoring), and patient breathing mechanics monitoring (the lung compliance and the airway resistance), etc., and it can be ended.

The Sputum Excretion Operation

During the sputum excretion, in each respiratory cycle, in the inspiratory stage, the control unit 5 controls the inspiratory branch 2 on, controls the expiratory branch 3 off, and controls the positive-pressure air supply to generate a positive-pressure injection air flow. Positive-pressure air is injected into the lungs of the patient through the inspiratory branch 2 and the patient interface air path 1. A positive-pressure ventilation pressure for sputum excretion is applied to the airway of the patient or lungs of the patient is filled with a positive-pressure inspiratory tidal volume for sputum excretion. In the expiratory stage, the inspiratory branch 2 is off, and the expiratory branch 3 is on. The control unit 5 controls the negative-pressure air supply to generate a negative-pressure air flow. A negative-pressure ventilation pressure for sputum excretion is applied to the airway of the patient. When the patient exhales through its own strength, the negative-pressure air supply generates the negative-pressure air flow, which increases expiratory air flow of the patient and brings out the sputum in the airway. The control unit 5 may also alternatively start the intrapulmonary percussive unit 8 during the sputum excretion operation.

Stopping of the sputum excretion: the sputum excretion may be stopped with following conditions. The stopping by time setting may be preferably executed. That is, the final duration of each sputum excretion operation may not exceed the specified set time, so as to prevent the long-term sputum excretion operation from causing injure to the patient.

Manually stopping the sputum excretion: an operator manually stops the sputum excretion.

By time setting: the sputum excretion is stopped when the duration of the sputum excretion operation reaches a preset time period.

Stopping as needed: the control unit 5 determines that the sputum excretion of the patient is completed by means of the oxygen saturation monitoring, the breath-sounds monitoring (including lung rales monitoring), and patient breathing mechanics monitoring (the lung compliance and the airway resistance), etc.

In conclusion, the non-invasive ventilator in this embodiment solves the clinical problem faced when assisting the patient with non-invasive ventilation to discharge sputum. Solving this problem may not only reduce the number of invasive ventilation, but also improve the success rate of switching from invasive ventilation to non-invasive ventilation for a patient who is intubated. In this way, on the one hand, the level of care for the patient with non-invasive ventilation may be greatly improved. On the other hand, waste of medical resources may be reduced. In addition, combined with the preliminary sputum excretion operation, it can make subsequent sputum excretion of the patient smoother and reduce the number of sputum excretion operations.

The auxiliary sputum excretion method for a non-invasive ventilator and the non-invasive ventilator of the present disclosure are not limited to the above-mentioned examples combining the above-mentioned embodiment one to embodiment four.

For example, the criterion for the non-invasive ventilator or the control unit 5 to determine whether the patient needs the sputum excretion is not limited to the oxygen saturation, the airway resistance, the lung compliance and the breath sounds. In various embodiments of the present disclosure, one or more of the oxygen saturation, the airway resistance, the lung compliance, and the breath sounds may be used as the criterion. Other parameters not mentioned in the above-mentioned embodiments but can be known to those skilled in the art to be able to determine whether the patient needs the sputum excretion based on common knowledge may also be used as the criterion.

For example, when the oxygen saturation of the patient is taken as the criterion, it is not limited to taking the oxygen saturation of the patient being less than the set value of oxygen saturation for initiating sputum excretion as the criterion, parameters not mentioned in the above-mentioned embodiments but can be known to those skilled in the art to be able to determine whether the patient needs the sputum excretion based on common knowledge may also be used as the criterion.

For example, when the airway resistance of the patient is taken as the criterion, it is not limited to taking the airway resistance of the patient being greater than the normal airway resistance level by the set value of airway resistance for initiating the sputum excretion for a certain time period as the criterion, parameters not mentioned in the above-mentioned embodiments but can be known to those skilled in the art to be able to determine whether the patient needs the sputum excretion based on common knowledge may also be used as the criterion.

For example, when the lung compliance of the patient is taken as the criterion, it is not limited to taking the lung compliance of the patient being less than the normal lung compliance level by the set value of lung compliance for initiating the sputum excretion for a certain time period as the criterion, parameters not mentioned in the above-mentioned embodiments but can be known to those skilled in the art to be able to determine whether the patient needs the sputum excretion based on common knowledge may also be used as the criterion.

For example, when the breath sounds of the patient is taken as the criterion, it is not limited to take followings as the criterion: detecting the moist rales, the time proportion of the moist rales in a respiratory cycle being greater than the set proportion of moist rales for initiating the sputum excretion, the frequency of the moist rales in different respiratory cycles being greater than the set frequency of moist rales for initiating the sputum excretion, and the value of the moist rales being greater than the set value of moist rales for initiating the sputum excretion as the criterion, parameters not mentioned in the above-mentioned embodiments but can be known to those skilled in the art to be able to determine whether the patient needs the sputum excretion based on common knowledge may also be used as the criterion.

For example, the criterion for the non-invasive ventilator or the control unit 5 to determine whether the patient needs to stop the sputum excretion is not limited to the oxygen saturation, the airway resistance, the lung compliance, and the breath sounds. In various embodiments of the present disclosure, one or more of the oxygen saturation, the airway resistance, the lung compliance, and the breath sounds may be used as the criterion. Other parameters not mentioned in the above-mentioned embodiments but can be known to those skilled in the art to be able to determine whether the patient needs to stop the sputum excretion based on common knowledge may also be used as the criterion.

For example, when the oxygen saturation of the patient is taken as the criterion, it is not limited to taking the oxygen saturation of the patient being greater than or equal to the set value of oxygen saturation for stopping sputum excretion as the criterion, parameters not mentioned in the above-mentioned embodiments but can be known to those skilled in the art to be able to determine whether the patient needs to stop the sputum excretion based on common knowledge may also be used as the criterion.

For example, when the airway resistance is taken as the criterion, it is not limited to taking the airway resistance of the patient to reach the normal airway resistance level as the criterion, parameters not mentioned in the above-mentioned embodiments but can be known to those skilled in the art to be able to determine whether the patient needs to stop the sputum excretion based on common knowledge may also be used as the criterion.

For example, when the lung compliance is taken as the criterion, it is not limited to taking the lung compliance of the patient to reach the normal lung compliance level as the criterion, parameters not mentioned in the above-mentioned embodiments but can be known to those skilled in the art to be able to determine whether the patient needs to stop the sputum excretion based on common knowledge may also be used as the criterion.

For example, when the breath sounds is taken as the criterion, it is not limited to taking the following as the criterion: no moist rales being detected, or the proportion of moist rales in a respiratory cycle being less than the set proportion of moist rales for stopping the sputum excretion, or the frequency of the moist rales in different respiratory cycles being less than the set frequency of moist rales for stopping the sputum excretion, or the value of the moist rales being less than the set value of moist rales for stopping the sputum excretion, in which, the set proportion of moist rales for stopping the sputum excretion is less than the set proportion of moist rales for initiating the sputum excretion, the set frequency of moist rales for stopping the sputum excretion is less than the set frequency of moist rales for initiating the sputum excretion, and the set value of moist rales for stopping the sputum excretion is less than the set value of moist rales for initiating the sputum excretion. Parameters not mentioned in the above-mentioned embodiments but can be known to those skilled in the art to be able to determine whether the patient needs to stop the sputum excretion based on common knowledge may also be used as the criterion.

For example, the criterion for the non-invasive ventilator or the control unit 5 to determine whether the patient needs the preliminary sputum excretion is not limited to the breath sounds. In various embodiments of the present disclosure, one or more of the oxygen saturation, the airway resistance, the lung compliance, and the breath sounds may be used as the criterion. Other parameters not mentioned in the above-mentioned embodiments but can be known to those skilled in the art to be able to determine whether the patient needs the preliminary sputum excretion based on common knowledge may also be used as the criterion.

For example, when the breath sounds is taken as the criterion, it is not limited to taking the followings as the criterion: the breath sounds being the medium moist rales or fine moist rales, the time proportion of the medium moist rales or the fine moist rales in a respiratory cycle being greater than the set proportion of medium moist rales or fine moist rales for initiating the preliminary sputum excretion, the frequency of the medium moist rales or the fine moist rales in different respiratory cycles being greater than the set frequency of medium moist rales or fine moist rales for initiating the preliminary sputum excretion, the value of the medium moist rales or the fine moist rales being greater than the set value of medium moist rales or fine moist rales for initiating the preliminary sputum excretion, and no coarse moist rales being detected. Parameters not mentioned in the above-mentioned embodiments but can be known to those skilled in the art to be able to determine whether the patient needs the preliminary sputum excretion based on common knowledge may also be used as the criterion.

For example, the criterion for the non-invasive ventilator or the control unit 5 to determine whether the patient needs to stop the preliminary sputum excretion is not limited to the oxygen saturation, the airway resistance, and the breath sounds. One or more of the oxygen saturation, the airway resistance, and the breath sounds may be used as the criterion. Other parameters not mentioned in the above-mentioned embodiments but can be known to those skilled in the art to be able to determine whether the patient needs to stop the preliminary sputum excretion based on common knowledge may also be used as the criterion.

For example, when the oxygen saturation is taken as the criterion, it is not limited to taking the oxygen saturation being less than the set value of oxygen saturation for stopping the preliminary sputum excretion, parameters not mentioned in the above-mentioned embodiments but can be known to those skilled in the art to be able to determine whether the patient needs to stop the preliminary sputum excretion based on common knowledge may also be used as the criterion.

For example, when the airway resistance is taken as the criterion, it is not limited to taking the airway resistance of the patient being increased by the set increment of airway resistance for stopping the preliminary sputum excretion compared with airway resistance when the patient needs the sputum excretion as the criterion, parameters not mentioned in the above-mentioned embodiments but can be known to those skilled in the art to be able to determine whether the patient needs to stop the preliminary sputum excretion based on common knowledge may also be used as the criterion.

For example, when the breath sounds is taken as the criterion, it is not limited to taking the followings as the criterion: coarse moist rales being detected, the time proportion of the coarse moist rales in a respiratory cycle being greater than the set proportion of coarse moist rales for stopping the preliminary sputum excretion, the frequency of the coarse moist rales in different respiratory cycles being greater than the set frequency of coarse moist rales for stopping the preliminary sputum excretion, and the value of the coarse moist rales being greater than the set value of coarse moist rales for stopping the preliminary sputum excretion. Parameters not mentioned in the above-mentioned embodiments but can be known to those skilled in the art to be able to determine whether the patient needs to stop the preliminary sputum excretion based on common knowledge may also be used as the criterion.

For example, the sputum excretion operation is not limited to applying a positive-pressure ventilation pressure for sputum excretion to airway of the patient or filling lungs of the patient with a positive-pressure inspiratory tidal volume for sputum excretion in an inspiratory stage, and applying a negative-pressure ventilation pressure for sputum excretion to the airway of the patient in an expiratory stage.

For example, the normal mechanical ventilation is not limited to the above-mentioned use of positive-pressure air supply for air injection and the voluntary exhalation of the patient when exhaling.

For example, the preliminary sputum excretion operation is not limited to the nebulization operation and the intrapulmonary percussion operation, and one of the two may be selected. The preliminary sputum excretion operation may also be auxiliary sputum excretion operations not mentioned in the above-mentioned embodiments but that can be known by those skilled in the art based on common knowledge.

Further, embodiments of the present disclosure disclose a non-transitory computer-readable storage medium. The storage medium has computer programs stored therein. When the computer programs are executed by a processor, an auxiliary sputum excretion method for a non-invasive ventilator according to any of the above-mentioned embodiments is implemented.

It should be noted that, in the description of the present disclosure, any process or method described in a flow chart or described herein in other ways may be understood to include one or more modules, segments or portions of codes of executable instructions for achieving specific logical functions or steps in the process, and the scope of a preferred embodiment of the present disclosure includes other implementations in which the order of execution is different from that which is depicted or discussed, including executing functions in a substantially simultaneous manner or in an opposite order according to the related functions, which should be understood by those skilled in the art.

The logic and/or step described in other manners herein or shown in the flow chart, for example, a particular sequence table of executable instructions for realizing the logical function, may be specifically achieved in any computer readable medium to be used by the instruction execution system, device or equipment (such as the system based on computers, the system comprising processors or other systems capable of obtaining the instruction from the instruction execution system, device and equipment and executing the instruction), or to be used in combination with the instruction execution system, device and equipment. As to the specification, "the computer readable medium" may be any device adaptive for including, storing, communicating, propagating or transferring programs to be used by or in combination with the instruction execution system, device or equipment. More specific examples of the computer readable medium comprise but are not limited to: an electronic connection (an electronic device) with one or more wires, a portable computer enclosure (a magnetic device), a random access memory (RAM), a read only memory (ROM), an erasable programmable read-only memory (EPROM or a flash memory), an optical fiber device and a portable compact disk read-only memory (CDROM). In addition, the computer readable medium may even be a paper or other appropriate medium capable of printing programs thereon, this is because, for example, the paper or other appropriate medium may be optically scanned and then edited, decrypted or processed with other appropriate methods when necessary to obtain the programs in an electric manner, and then the programs may be stored in the computer memories.

It would be understood by those skilled in the art that all or parts of the steps carried by the method in the above-described embodiments may be completed by commanding the related hardware with programs. The programs may be stored in a computer readable storage medium, and the programs include one or a combination of the steps in the method embodiments of the present disclosure when the program is executed.

In the description of the present disclosure, reference throughout this specification to "an embodiment," "some embodiments," "an example," "a specific example," or "some examples," means that a particular feature, structure, material, or characteristic described in connection with the embodiment or example is included in at least one embodiment or example of the present disclosure. Thus, the appearances of the above terms throughout this specification are not necessarily referring to the same embodiment or example of the present disclosure. Furthermore, the particular features, structures, materials, or characteristics may be combined in any suitable manner in one or more embodiments or examples. In addition, those skilled in the art can incorporate and combine the different embodiments or examples and the characteristics of the different embodiments or examples described in this specification without contradicting each other.

Although embodiments have been shown and described, it would be appreciated by those skilled in the art that the above embodiments are exemplary, and cannot be construed to limit the present disclosure, and changes, modifications, alternatives, and variations can be made of the above embodiments within the scope of the present disclosure.

What is claimed is:

1. An auxiliary sputum excretion method for a non-invasive ventilator, comprising:
    initiating a sputum excretion operation in each respiratory cycle of a patient after the non-invasive ventilator determines that the patient needs sputum excretion during a normal mechanical ventilation of the non-invasive ventilator for the patient;
    stopping the sputum excretion operation in response to determining that the patient needs to stop the sputum excretion;
    determining whether the patient needs preliminary sputum excretion after the non-invasive ventilator determines that the patient needs the sputum excretion; and
    performing a preliminary sputum excretion operation after the non-invasive ventilator determines that the patient needs the preliminary sputum excretion, and stopping the preliminary sputum excretion operation and performing the sputum excretion operation in each respiratory cycle of the patient in response to determining that the patient needs to stop the preliminary sputum excretion;
    wherein, the non-invasive ventilator performs the sputum excretion operation directly in each respiratory cycle of the patient in response to determining that the patient does not need the preliminary sputum excretion by the non-invasive ventilator;
    wherein, determining whether the patient needs preliminary sputum excretion comprises:
        determining, by the non-invasive ventilator, whether the patient needs the preliminary sputum excretion by using breath sounds as a criterion;

wherein, determining whether the patient needs the preliminary sputum excretion by using breath sounds as a criterion comprises:
monitoring, by the non-invasive ventilator, breath sounds of the patient and
determining, by the non-invasive ventilator, that the patient needs the preliminary sputum excretion in response to:
medium moist rales or fine moist rales being detected, a time proportion of the medium moist rales or the fine moist rales in a respiratory cycle being greater than a set proportion of medium moist rales or fine moist rales for initiating the preliminary sputum excretion, a frequency of the medium moist rales or the fine moist rales in different respiratory cycles being greater than a set frequency of medium moist rales or fine moist rales for initiating the preliminary sputum excretion, a value of the medium moist rales or the fine moist rales being greater than a set value of medium moist rales or fine moist rales for initiating the preliminary sputum excretion, and no coarse moist rales being detected.

2. The auxiliary sputum excretion method according to claim 1, further comprising at least one of:
determining, by the non-invasive ventilator, whether the patient needs the sputum excretion by using one or more of oxygen saturation, airway resistance, lung compliance, and breath sounds as a criterion;
determining, by the non-invasive ventilator, whether the patient needs to stop the sputum excretion by using one or more of oxygen saturation, airway resistance, lung compliance, and breath sounds as a criterion; and
determining, by the non-invasive ventilator, that the patient needs to stop the sputum excretion in response to determining that a duration after initiating the sputum excretion is greater than the upper time limit for stopping the sputum excretion, the upper time limit for stopping the sputum excretion being set by the non-invasive ventilator.

3. The auxiliary sputum excretion method according to claim 1, further comprising:
monitoring, by the non-invasive ventilator, oxygen saturation, airway resistance, lung compliance, and breath sounds of the patient,
wherein, determining, by the non-invasive ventilator, that the patient needs the sputum excretion comprises:
determining, by the non-invasive ventilator, that the patient needs the sputum excretion in response to any of following conditions being satisfied:
the oxygen saturation of the patient decreasing to a set value of oxygen saturation for initiating the sputum excretion, or decreasing by an oxygen saturation change value for initiating the sputum excretion;
the airway resistance of the patient being a set value of airway resistance for initiating the sputum excretion greater than a normal airway resistance level for a certain time period;
the lung compliance of the patient being a set value of lung compliance for initiating the sputum excretion less than a normal lung compliance level for a certain time period; and
moist rales being detected, a time proportion of the moist rales in a respiratory cycle being greater than a set proportion of moist rales for initiating the sputum excretion, a frequency of the moist rales in different respiratory cycles being greater than a set frequency of moist rales for initiating the sputum excretion, and a value of the moist rales being greater than a set value of moist rales for initiating the sputum excretion; and
determining, by the non-invasive ventilator, that the patient needs to stop the sputum excretion comprises:
determining, by the non-invasive ventilator, that the patient needs to stop the sputum excretion in response to following conditions being satisfied:
the oxygen saturation of the patient being greater than or equal to a set value of oxygen saturation for stopping the sputum excretion, the set value of oxygen saturation for stopping the sputum excretion being greater than the set value of oxygen saturation for initiating the sputum excretion;
the airway resistance of the patient reaching the normal airway resistance level;
the lung compliance of the patient reaching the normal lung compliance level; and
at least one of: no moist rales being detected, a proportion of moist rales in a respiratory cycle being less than a set proportion of moist rales for stopping the sputum excretion, a frequency of the moist rales in different respiratory cycles being less than a set frequency of moist rales for stopping the sputum excretion, and a value of the moist rales being less than a set value of moist rales for stopping the sputum excretion, wherein, the set proportion of moist rales for stopping the sputum excretion is less than the set proportion of moist rales for initiating the sputum excretion, the set frequency of moist rales for stopping the sputum excretion is less than the set frequency of moist rales for initiating the sputum excretion, and the set value of moist rales for stopping the sputum excretion is less than the set value of moist rales for initiating the sputum excretion.

4. The auxiliary sputum excretion method according to claim 1, wherein, determining whether the patient needs preliminary sputum excretion further comprises at least one of:
determining, by the non-invasive ventilator, whether the patient needs to stop the preliminary sputum excretion by using one or more of oxygen saturation, airway resistance, and breath sounds as a criterion; and
determining, by the non-invasive ventilator, that the patient needs to stop the preliminary sputum excretion in response to determining that a duration after initiating the preliminary sputum excretion is greater than an upper time limit for stopping the preliminary sputum excretion, the upper time limit for stopping the preliminary sputum excretion be set by the non-invasive ventilator.

5. The auxiliary sputum excretion method according to claim 4, further comprising:
monitoring, by the non-invasive ventilator, the oxygen saturation, the airway resistance, and the breath sounds of the patient,
wherein, determining that the patient needs to stop the preliminary sputum excretion comprises: determining that the patient needs to stop the preliminary sputum excretion in response to any of following conditions being satisfied:
the oxygen saturation of the patient being less than a set value of oxygen saturation for stopping the preliminary sputum excretion, the set value of oxygen saturation for stopping the preliminary sputum excretion being less than the set value of oxygen saturation for initiating the sputum excretion;

the airway resistance of the patient being increased by a set increment of airway resistance for stopping the preliminary sputum excretion compared with airway resistance when the patient needs the sputum excretion; and coarse moist rales being detected, a time proportion of the coarse moist rales in a respiratory cycle being greater than a set proportion of coarse moist rales for stopping the preliminary sputum excretion, a frequency of the coarse moist rales in different respiratory cycles being greater than a set frequency of coarse moist rales for stopping the preliminary sputum excretion, and a value of the coarse moist rales being greater than a set value of coarse moist rales for stopping the preliminary sputum excretion.

6. The auxiliary sputum excretion method according to claim 1, wherein, the sputum excretion operation comprises: applying a positive-pressure ventilation pressure for sputum excretion to airway of the patient or filling lungs of the patient with a positive-pressure inspiratory tidal volume for sputum excretion in an inspiratory stage, and applying a negative-pressure ventilation pressure for sputum excretion to the airway of the patient in an expiratory stage; and the preliminary sputum excretion operation comprises: a nebulization operation and/or an intrapulmonary percussive operation.

7. A non-invasive ventilator, comprising an inspiratory branch and an expiratory branch, and further comprising:

a positive-pressure air supply, arranged on the inspiratory branch;

a negative-pressure air supply, arranged on the expiratory branch;

a sensor, configured to monitor physiological data for determining whether a patient needs sputum excretion and whether the patient needs to stop sputum excretion; and a controller, communicated and connected with the positive-pressure air supply, the negative-pressure air supply, and the sensor, and configured to:

determine whether the patient needs sputum excretion and whether the patient needs to stop the sputum excretion by analyzing the physiological data monitored by the sensor, in response to determining that the patient needs the sputum excretion, control the positive-pressure air supply to apply a positive-pressure ventilation pressure for sputum excretion to airway of the patient or to fill lungs of the patient with a positive- pressure inspiratory tidal volume for sputum excretion every time the patient being in an inspiratory stage, and control the negative-pressure air supply to apply a negative- pressure ventilation pressure for sputum excretion to the airway of the patient every time the patient being in an expiratory stage, and stop the positive-pressure air supply applying the positive-pressure ventilation pressure for sputum excretion to the airway of the patient or filling the lungs of the patient with the positive-pressure inspiratory tidal volume for sputum excretion every time the patient being in the inspiratory stage, and stop the negative-pressure air supply applying the negative-pressure ventilation pressure for sputum excretion to the airway of the patient every time the patient being in the expiratory stage in response to determining that the patient needs to stop the sputum excretion;

a nebulizer and/or an intrapulmonary percussive device, wherein, the nebulizer and/or the intrapulmonary percussive device is communicated and connected with the controller;

the controller is configured to: determine whether the patient needs preliminary sputum excretion or whether the patient needs to stop the preliminary sputum excretion by analyzing the physiological data monitored by the sensor, the controller determining whether the patient needs the preliminary sputum excretion after determining that the patient needs the sputum excretion, start the nebulizer and/or the intrapulmonary percussive device in response to determining that the patient needs the preliminary sputum excretion, stop the nebulizer and/or the intrapulmonary percussive device in response to determining that the patient needs to stop the preliminary sputum excretion, and perform the operation of controlling the positive-pressure air supply to apply the positive-pressure ventilation pressure for sputum excretion to the airway of the patient or filling the lungs of the patient with the positive-pressure inspiratory tidal volume for sputum excretion every time the patient being in the inspiratory stage, and controlling the negative-pressure air supply to apply the negative-pressure ventilation pressure for sputum excretion to the airway of the patient every time the patient being in the expiratory stag, wherein the controller is configured to directly perform, in response to determining that the patient does not need the preliminary sputum excretion, the operation of controlling the positive-pressure air supply to apply the positive-pressure ventilation pressure for sputum excretion to the airway of the patient or filling the lungs of the patient with the positive-pressure inspiratory tidal volume for sputum excretion every time the patient being in the inspiratory stage, and controlling the negative-pressure air supply to apply the negative-pressure ventilation pressure for sputum excretion to the airway of the patient every time the patient being in the expiratory stage;

wherein, the sensor is configured to monitor physiological data for obtaining oxygen saturation, airway resistance, lung compliance, and breath sounds of the patient wherein the controller is configured to determine that the patient needs the preliminary sputum excretion in response to following conditions being satisfied:

medium moist rales or fine moist rales being detected, a time proportion of the medium moist rales or the fine moist rales in a respiratory cycle being greater than a set proportion of medium moist rales or fine moist rales for initiating the preliminary sputum excretion, a frequency of the medium moist rales or the fine moist rales in different respiratory cycles being greater than a set frequency of medium moist rales or fine moist rales for initiating the preliminary sputum excretion, a value of the medium moist rales or the fine moist rales being greater than a set value of medium moist rales or fine moist rales for initiating the preliminary sputum excretion, and no coarse moist rales being detected.

8. The non-invasive ventilator according to claim 7, wherein, the controller is configured to determine that the patient needs the sputum excretion in response to any of following conditions being satisfied:

the oxygen saturation of the patient decreasing to a set value of oxygen saturation for initiating the sputum excretion, or decreasing by an oxygen saturation change value for initiating the sputum excretion;

the airway resistance of the patient being a set value of airway resistance for initiating the sputum excretion greater than a normal airway resistance level for a certain time period;

the lung compliance of the patient being a set value of lung compliance for initiating the sputum excretion less than a normal lung compliance level for a certain time period; and moist rales being detected, a time proportion of the moist rales in a respiratory cycle being greater than a set proportion of moist rales for initiating the sputum excretion, a frequency of the moist rales in different respiratory cycles being greater than a set frequency of moist rales for initiating the sputum excretion, and a value of the moist rales being greater than a set value of moist rales for initiating the sputum excretion.

9. The non-invasive ventilator according to claim 7, wherein, the sensor is configured to monitor physiological data for obtaining oxygen saturation, airway resistance, lung compliance, and breath sounds of the patient.

10. The non-invasive ventilator according to claim 9, wherein the controller is configured to determine that the patient needs to stop the sputum excretion in response to following conditions being satisfied:

the oxygen saturation of the patient being greater than or equal to a set value of oxygen saturation for stopping the sputum excretion, the set value of oxygen saturation for stopping the sputum excretion being greater than the set value of oxygen saturation for initiating the sputum excretion;

the airway resistance of the patient reaching the normal airway resistance level;

the lung compliance of the patient reaching the normal lung compliance level; and at least one of: no moist rales being detected, a proportion of moist rales in a respiratory cycle being less than a set proportion of moist rales for stopping the sputum excretion, a frequency of the moist rales in different respiratory cycles being less than a set frequency of moist rales for stopping the sputum excretion, and a value of the moist rales being less than a set value of moist rales for stopping the sputum excretion, wherein, the set proportion of moist rales for stopping the sputum excretion is less than the set proportion of moist rales for initiating the sputum excretion, the set frequency of moist rales for stopping the sputum excretion is less than the set frequency of moist rales for initiating the sputum excretion, and the set value of moist rales for stopping the sputum excretion is less than the set value of moist rales for initiating the sputum excretion.

11. The non-invasive ventilator according to claim 9, wherein the controller is further configured to set an upper time limit for stopping the sputum excretion, the controller is configured to determine that the patient needs to stop the sputum excretion in response to determining that the patient needs to stop the sputum excretion in response to determining that a duration after initiating the sputum excretion is greater than the upper time limit for stopping the sputum excretion.

12. The non-invasive ventilator according to claim 7, wherein the controller is configured to determine that the patient needs to stop the preliminary sputum excretion in response to any of following conditions being satisfied:

the oxygen saturation of the patient being less than a set value of oxygen saturation for stopping the preliminary sputum excretion, the set value of oxygen saturation for stopping the preliminary sputum excretion being less than the set value of oxygen saturation for initiating the sputum excretion;

the airway resistance of the patient being increased by a set increment of airway resistance for stopping the preliminary sputum excretion compared with airway resistance when the patient needs the sputum excretion;

coarse moist rales being detected, a time proportion of the coarse moist rales in a respiratory cycle being greater than a set proportion of coarse moist rales for stopping the preliminary sputum excretion, a frequency of the coarse moist rales in different respiratory cycles being greater than a set frequency of coarse moist rales for stopping the preliminary sputum excretion, and a value of the coarse moist rales being greater than a set value of coarse moist rales for stopping the preliminary sputum excretion.

13. The non-invasive ventilator according to claim 7, wherein the controller is further configured to set an upper time limit for stopping the preliminary sputum excretion, and the controller is configured to determine that the patient needs to stop the preliminary sputum excretion in response to determining that a duration after initiating the preliminary sputum excretion is greater than the upper time limit for stopping the preliminary sputum excretion.

14. A non-transitory computer-readable storage medium having a computer program stored thereon, wherein when the program is executed by a processor, an auxiliary sputum excretion method for a non-invasive ventilator is implemented, the method comprising:

initiating a sputum excretion operation in each respiratory cycle of a patient after the non-invasive ventilator determines that the patient needs sputum excretion during a normal mechanical ventilation of the non-invasive ventilator for the patient; and stopping the sputum excretion operation in response to determining that the patient needs to stop the sputum excretion;

determining whether the patient needs preliminary sputum excretion after the non-invasive ventilator determines that the patient needs the sputum excretion; and performing a preliminary sputum excretion operation after the non-invasive ventilator determines that the patient needs the preliminary sputum excretion, and stopping the preliminary sputum excretion operation and performing the sputum excretion operation in each respiratory cycle of the patient in response to determining that the patient needs to stop the preliminary sputum excretion;

wherein, the non-invasive ventilator performs the sputum excretion operation directly in each respiratory cycle of the patient in response to determining that the patient does not need the preliminary sputum excretion by the non-invasive ventilator;

wherein, determining whether the patient needs preliminary sputum excretion comprises:

determining, by the non-invasive ventilator, whether the patient needs the preliminary sputum excretion by using breath sounds as a criterion;

wherein, determining whether the patient needs the preliminary sputum excretion by using breath sounds as a criterion comprises:

monitoring, by the non-invasive ventilator, breath sounds of the patient, determining, by the non-invasive ventilator, that the patient needs the preliminary sputum excretion in response to:
  medium moist rales or fine moist rales being detected, a time proportion of the medium moist rales or the fine moist rales in a respiratory cycle being greater than a set proportion of medium moist rales or fine moist rales for initiating the preliminary sputum excretion, a frequency of the medium moist rales or the fine moist rales in different respiratory cycles being greater than a set frequency of medium moist rales or fine moist rales for initiating the preliminary sputum excretion, a value of the medium moist rales or the fine moist rales being greater than a set value of medium moist rales or fine moist rales for initiating the preliminary sputum excretion, and no coarse moist rales being detected.

15. The storage medium according to claim 14, wherein the method further comprises at least one of:
  determining, by the non-invasive ventilator, whether the patient needs the sputum excretion by using one or more of oxygen saturation, airway resistance, lung compliance, and breath sounds as a criterion; and/or
  determining, by the non-invasive ventilator, whether the patient needs to stop the sputum excretion by using one or more of oxygen saturation, airway resistance, lung compliance, and breath sounds as a criterion; and/or
  determining, by the non-invasive ventilator, that the patient needs to stop the sputum excretion in response to determining that a duration after initiating the sputum excretion is greater than an upper time limit for stopping the sputum excretion, the upper time limit for stopping the sputum excretion being set by the non-invasive ventilator.

16. The storage medium according to claim 14, wherein, the method further comprises:
  monitoring, by the non-invasive ventilator, oxygen saturation, airway resistance, lung compliance, and breath sounds of the patient, determining, by the non-invasive ventilator, that the patient needs the sputum excretion comprises: determining, by the non-invasive ventilator, that the patient needs the sputum excretion in response to any of following conditions being satisfied:
    the oxygen saturation of the patient decreasing to a set value of oxygen saturation for initiating the sputum excretion, or decreasing by an oxygen saturation change value for initiating the sputum excretion;
    the airway resistance of the patient being a set value of airway resistance for initiating the sputum excretion greater than a normal airway resistance level for a certain time period;
    the lung compliance of the patient being a set value of lung compliance for initiating the sputum excretion less than a normal lung compliance level for a certain time period; and
    moist rales being detected, a time proportion of the moist rales in a respiratory cycle being greater than a set proportion of moist rales for initiating the sputum excretion, a frequency of the moist rales in different respiratory cycles being greater than a set frequency of moist rales for initiating the sputum excretion, and a value of the moist rales being greater than a set value of moist rales for initiating the sputum excretion; and
  determining, by the non-invasive ventilator, that the patient needs to stop the sputum excretion comprises:
  determining, by the non-invasive ventilator, that the patient needs to stop the sputum excretion in response to following conditions being satisfied:
    the oxygen saturation of the patient being greater than or equal to a set value of oxygen saturation for stopping the sputum excretion, the set value of oxygen saturation for stopping the sputum excretion being greater than the set value of oxygen saturation for initiating the sputum excretion;
    the airway resistance of the patient reaching the normal airway resistance level;
    the lung compliance of the patient reaching the normal lung compliance level; and
    at least one of: no moist rales being detected, a proportion of moist rales in a respiratory cycle being less than a set proportion of moist rales for stopping the sputum excretion, a frequency of the moist rales in different respiratory cycles being less than a set frequency of moist rales for stopping the sputum excretion, and a value of the moist rales being less than a set value of moist rales for stopping the sputum excretion, wherein, the set proportion of moist rales for stopping the sputum excretion is less than the set proportion of moist rales for initiating the sputum excretion, the set frequency of moist rales for stopping the sputum excretion is less than the set frequency of moist rales for initiating the sputum excretion, and the set value of moist rales for stopping the sputum excretion is less than the set value of moist rales for initiating the sputum excretion.

* * * * *